(12) United States Patent
Rubin et al.

(10) Patent No.: US 11,224,385 B2
(45) Date of Patent: Jan. 18, 2022

(54) METHOD FOR DETERMINING A PERSON'S SLEEPING PHASE WHICH IS FAVOURABLE FOR WAKING UP

(71) Applicant: Healbe Corporation, Redwood City, CA (US)

(72) Inventors: Mikhail S. Rubin, St. Petersburg (RU); Yury V. Sviryaev, St. Petersburg (RU)

(73) Assignee: HEALBE CORPORATION, Redwood City, CA (US)

( * ) Notice: Subject to any disclaimer, the term of this patent is extended or adjusted under 35 U.S.C. 154(b) by 124 days.

(21) Appl. No.: 14/865,879

(22) Filed: Sep. 25, 2015

(65) Prior Publication Data

US 2016/0007931 A1   Jan. 14, 2016

Related U.S. Application Data

(63) Continuation of application No. PCT/RU2014/000237, filed on Apr. 2, 2014.

(51) Int. Cl.
*A61B 5/00* (2006.01)
*A61B 5/024* (2006.01)
(Continued)

(52) U.S. Cl.
CPC .......... *A61B 5/7235* (2013.01); *A61B 5/0205* (2013.01); *A61B 5/02438* (2013.01);
(Continued)

(58) Field of Classification Search
CPC ... A61B 5/7235; A61B 5/0205; A61B 5/0456; A61B 5/0816; A61B 5/11; A61B 5/4812; A61B 5/0452
See application file for complete search history.

(56) References Cited

U.S. PATENT DOCUMENTS 4,306,567 A * 12/1981 Krasner ............... A61B 5/0816
600/484
5,280,791 A    1/1994 Lavie
(Continued)

FOREIGN PATENT DOCUMENTS

DE      4209336 A1    9/1993
JP    2003260040 A    9/2003
(Continued)

OTHER PUBLICATIONS

Miele "Polysonmography," http://www.zonasna.ru/serv002.html, Feb. 21, 2010.
(Continued)

*Primary Examiner* — Devin B Henson
*Assistant Examiner* — Raymond P Dulman
(74) *Attorney, Agent, or Firm* — Patentbar International, P.C.

(57) ABSTRACT

A pulse wave signal is registered and an occurrence of human limb movements detected during sleep using a pulse wave sensor and an accelerometer. The values of RR intervals and respiratory rate are measured at preset time intervals $\Delta t_i$ based on pulse wave signal. Mean $P_1$, minimal $P_2$, and maximal $P_3$ values of RR intervals, the standard deviation of RR intervals $P_4$, average respiratory rate $P_5$ and average number of limb movements $P_6$ are determined based on the above measured values. Function value $F(\Delta t_i)$ is determined thereafter as:

$$F(\Delta t_i) = -K_1 P_1 - K_2 P_2 - K_3 P_3 + K_4 P_4 + K_5 P_5 + K_6 P_6,$$

where $K_1$-$K_6$ are weight coefficients characterizing the contribution of the corresponding parameter to function value $F(\Delta t_i)$; whereat the onset and termination of sleep phase favorable to awakening is determined by increments of function $F(\Delta t_i)$.

15 Claims, 3 Drawing Sheets

(51) Int. Cl.
  *A61B 5/08*      (2006.01)
  *G04G 13/02*     (2006.01)
  *A61B 5/352*     (2021.01)
  *A61B 5/0205*    (2006.01)
  *A61B 5/11*      (2006.01)
  *G04C 3/00*      (2006.01)
  *A61B 5/349*     (2021.01)

(52) U.S. Cl.
  CPC .............. *A61B 5/0816* (2013.01); *A61B 5/11* (2013.01); *A61B 5/352* (2021.01); *A61B 5/4812* (2013.01); *A61B 5/681* (2013.01); *G04G 13/023* (2013.01); *A61B 5/349* (2021.01); *G04C 3/001* (2013.01)

(56) References Cited

U.S. PATENT DOCUMENTS

| | | | |
|---|---|---|---|
| 2004/0034289 A1* | 2/2004 | Teller | A61B 5/02055 600/300 |
| 2005/0190065 A1 | 9/2005 | Ronnholm | |
| 2006/0111635 A1 | 5/2006 | Todros et al. | |
| 2006/0241510 A1* | 10/2006 | Halperin | A61B 5/113 600/534 |
| 2008/0269625 A1 | 10/2008 | Halperin et al. | |
| 2009/0203972 A1* | 8/2009 | Heneghan | A61B 5/0507 600/301 |
| 2011/0230790 A1 | 9/2011 | Kozlov | |
| 2011/0264164 A1* | 10/2011 | Christopherson | A61B 5/0803 607/42 |
| 2012/0083705 A1* | 4/2012 | Yuen | A61B 5/0002 600/508 |
| 2013/0261404 A1* | 10/2013 | Sato | A61B 5/4806 600/300 |
| 2014/0327515 A1* | 11/2014 | Luna | H04R 3/00 340/4.42 |
| 2015/0112606 A1* | 4/2015 | He | G06F 21/00 702/19 |

FOREIGN PATENT DOCUMENTS

| | | |
|---|---|---|
| KR | 20120045661 A | 5/2012 |
| RU | 2061406 C1 | 6/1996 |
| WO | 2007/143535 A2 | 12/2007 |

OTHER PUBLICATIONS

International Search Report from International Application No. PCT/RU2014/000237, filed Apr. 2, 2014, dated Aug. 28, 2014.
Tsiboulsky et al, On Functional Role of Paradoxical Phase of Sleep, The Central Mechanisms of Motivation and Sensory Processes: Coll. Art, 1988, pp. 113-120, Baku.
Gecht et al., Sleep-Wakefulness Cycle: Nightdreams and Health, Journal of New Medical Technologies, 1994, v. 1, No. 2, pp. 45-50.

* cited by examiner

METHOD FOR DETERMINING A PERSON'S SLEEPING PHASE WHICH IS FAVOURABLE FOR WAKING UP

RELATED APPLICATIONS

This application is a Continuation application of International Application PCT/RU2014/000237, filed on Apr. 2, 2014, which in turn claims priority to Russian Patent Application No. RU 2013116790, filed Apr. 5, 2013, both of which are incorporated herein by reference in their entirety.

FIELD OF INVENTION

The invention relates to the field of measurements of human condition parameters for diagnostic purposes, in particular to measurement of parameters characterizing human sleep.

BACKGROUND OF THE INVENTION

As is known, human sleep consists of alternating phases of the so-called non-REM and REM sleep. The above phases follow each other in cycles (typically from 4 to 6 cycles) during healthy human sleep. The experience has shown that the REM phase is the most favorable to awakening. However, a great many people wake up either to the signal of alarm clock set for a specific time, or are affected by other, random factors, which means their awakening not always occurs at an optimal sleep phase. Accordingly, to provide more comfortable living conditions for people, the development of simple, small and easy-to-use technical means designed to determine sleep phase optimal for awakening and providing control over wake-up devices generating a waking sound or other signal is important.

Various methods for determining human sleep phases, including those favorable to awakening, are known.

Medical studies have found that specific sleep phases can be identified with a sufficient confidence by registering various bioelectric signals, such as EEG characterizing the bioelectric activity of the brain, electromyogram reflecting muscle activity, or EOG characterizing changes in biopotential during eye movement. However, these methods are applicable only in healthcare institutions providing the assistance of specially trained personnel and cannot be used in everyday life. Furthermore, numerous internal and external factors affect human sleep, so one and the same person's sleep can proceed in different ways. Therefore, it becomes necessary that the phase favorable to awakening be determined for a given person on the basis of his/her current psychophysiological state and sleeping conditions.

Various methods and devices are known that are designed to awaken a person during a phase of sleep favorable thereto and based on current measurements of physiological parameters of the sleeping person.

Thus, patent RU 2061406 describes a method for waking up a person during a predetermined sleep phase. For this purpose, EEG is recorded during sleep by means of sensors to identify the current REM phase and the wake-up signal generated in a predetermined interval of time is synchronized with said EEG. EEG at REM sleep, according to the authors, is distinguished by desynchronization with the emergence of beta waves in the range of 18 Hz to 32 Hz and by low-amplitude mixed activity with theta waves present.

US Patent Application 20110230790 describes a method and device for waking up a person during a required sleep phase before a predetermined ultimate wake-up time, and for identifying the best time to go bed. REM phase is identified by the motor activity registered with accelerometer attached to human leg or arm.

US Patent Application 20050190065 describes a method for waking up a person in the sleep phase the most favorable thereto. According to the authors, REM phase is characterized by cardiac blood flow increase, poor thermoregulation of body (its temperature may rise or fall depending on the ambient temperature); vasoconstriction and reduction of vascular blood flow which can be measured by peripheral arterial blood pressure monitor; unstable and increased heart rate, blood pressure and respiratory rate.

The closest to the claimed invention is the method for waking up a person at optimal time within a preset period and during a favorable sleep phase, as described in patent DE 4,209,336. REM phase is identified by measuring heart rate, respiratory rate, bodily or head temperature, and detecting eye and body movements. Devices implementing said method can be made in the form of an armband, ear clip, chest belt, etc.

The analysis of known prior art shows that such devices are not capable of identifying the onset and termination of REM sleep with sufficient reliability or said devices create a practical inconvenience to a sleeping person due to a significant number of sensors attached to the person.

SUMMARY OF THE INVENTION

The task to be solved by the present invention is to provide a simple and reliable method for identifying a sleep phase favorable to awakening, i.e., REM sleep, and capable of being embodied a device easily attached onto a person and not disturbing person's sleep.

The method in accordance with the present invention enables the identification of human sleep phases favorable to awakening by registering a pulse wave signal and movement of human limbs using, respectively, a pulse wave sensor and at least one motion sensor attached onto a person during sleep, with said pulse wave signal serving as a basis for calculating the values RR intervals and respiratory rate; wherein the onset and termination of a sleep phase favorable to awakening are identified by function increment $F(\Delta t_i)$ whose values are determined over given time intervals $\Delta t_i$, where i is the serial number of the time interval; said function increments being expressed as:

$$F(\Delta t_i) = -K_1 P_1 - K_2 P_2 - K_3 P_3 + K_4 P_4 + K_5 P_5 K_6 P_6, \qquad (1)$$

where:

$P_1$ is the mean value of RR intervals over time interval $\Delta t_i$;

$P_2$ is the minimum value of RR intervals over time interval $\Delta t_i$;

$P_3$ is the maximum value of RR intervals over time interval $\Delta t_i$;

$P_4$ is standard deviation of RR intervals over the preceding time interval of 3-20 min;

$P_5$ is the mean value of respiratory rate over time interval $\Delta t_i$;

$P_6$ is the average number of detected limb movements over the preceding period of 0.5-10 minutes;

$K_1$-$K_6$ are weight coefficients characterizing the contribution of corresponding parameter $P_1$-$P_6$ to function value $F(\Delta t_i)$.

The certainty and reliability of identification of sleep phase favorable to awakening is defined by the fact experimentally established by the inventors that selected parameters $P_1$-$P_6$ are informative and allow, when combined, to identify the onset and termination of REM phase. On the other hand, all these parameters are determined solely by registering pulse wave signal and movements of human limbs, which requires such sensors that would not disturb human sleep when attached onto human body. Also important is the fact that the selected parameters are members of equation (1) with certain weight coefficients $K_1$-$K_6$ which can also be determined experimentally, thus making it possible to obtain function values $F(\Delta t_i)$ which provide a reliable identification of the onset and termination of phase favorable to human awakening.

The limits of the time interval over which the values of parameter $P_4$ (standard deviation of RR intervals) are measured have been established experimentally, so:

if the time interval is less than 3 minutes, the probability of the so-called Type I error ("false alarm") grows unacceptably;

if the time interval is more than 20 minutes, the probability of the so-called Type II error ("missing the target") grows unacceptably.

The time interval during which the value of parameter $P_4$ is measured should be selected preferably in the range from 4 minutes to 6 minutes.

The limits of the time interval during which the value of parameter $P_6$ (mean value of respiratory rate) is measured have also been established experimentally, so:

if the time interval is less than 0.5 minutes, the probability of Type I error grows unacceptably;

if the time interval is more than 10 minutes, the probability of Type II error grows unacceptably.

The time interval during which the value of parameter $P_6$ is determined should be selected preferably in the range from 4 minutes to 6 minutes.

In particular, the following values of weight coefficients for healthy people have been experimentally determined:

for parameter $P_1$ measured in ms, the value of weight coefficient $K_1$ may be selected in the range from 0.6 $ms^{-1}$ to 3 $ms^{-1}$, preferably from 0.9 $ms^{-1}$ to 1.05 $ms^{-1}$;

for parameter $P_2$, measured in ms, the value of weight coefficient $K_2$ may be selected in the range from 0.1 $ms^{-1}$ to 0.7 $ms^{-1}$, preferably from 0.1 $ms^{-1}$ to 0.2 $ms^{-1}$;

for parameter $P_3$, measured in ms, the value of weight coefficient $K_3$ may be selected in the range from 0.01 $ms^{-1}$ to 0.3 $ms^{-1}$, preferably from 0.02 $ms^{-1}$ to 0.05 $ms^{-1}$;

for parameter $P_4$, measured in ms, the value of weight coefficient $K_4$ may be selected in the range from 0.5 $ms^{-1}$ to 3 $ms^{-1}$, preferably from 1.3 $ms^{-1}$ to 1.5 $ms^{-1}$;

for parameter $P_5$, measured in $min^{-1}$, the value of weight coefficient $K_5$ may be selected in the range from 1 min to 10 min, preferably from 1.5 min to 2.3 min;

for parameter $P_6$ the value of weight coefficient $K_6$ can be selected in the range from 5 to 50, preferably from 18 to 24.

In particular implementations of the method, pulse wave may be registered using piezoelectric sensor, strain gage, or optical sensor fixed on the wrist or forearm, while the motion detector can be represented by an accelerometer fixed on the arm or leg.

Time intervals $\Delta t_i$ may be selected in the range from 1 minute to 6 minutes.

In particular, the onset of sleep phase favorable to awakening is identified if the increment of function $F(\Delta t_i)$ over time period $\Delta t_i$ exceeds a first preset threshold value.

In particular, the end of sleep phase favorable to awakening is identified if the increment of function $F(\Delta t_i)$ over time period $\Delta t_i$ becomes less than a second preset threshold value.

BRIEF DESCRIPTION OF DRAWINGS

The invention is illustrated by the following graphic materials:

FIG. 1a shows a graph of function $F(\Delta t_i)$ for one of the registered REM phases, while FIG. 1b shows a graph $\Delta F(\Delta t_i)$ of function increment $F(\Delta t_i)$, shown in FIG. 1a;

FIG. 6 shows the device from the outside, where the indicator is located.

DETAILED DESCRIPTION OF THE PREFERRED EMBODIMENTS

A method for determining the sleep phase favorable to awakening can be implemented using two sensors: a pulse wave sensor and a sensor capable of responding to arm or leg movement, i.e., a motion sensor such as an accelerometer. The sensors can be mounted on a human body separately from each other. For example, the motion sensor can be attached to an arm or a leg, while the pulse wave sensor onto the wrist or forearm. Pulse wave sensors may be represented by piezoelectric sensors, strain gages, and optical sensors. The use of an optical sensor or photoplethysmographic sensor sensitive to vascular blood filling of bodily areas is preferable. It is more convenient for the user if both pulse wave sensor and motion sensor are mounted in a single device, such as shown in FIG. 5 and FIG. 6 and made in the form of bracelet 1 to be worn on the wrist.

Figures 5, 6:
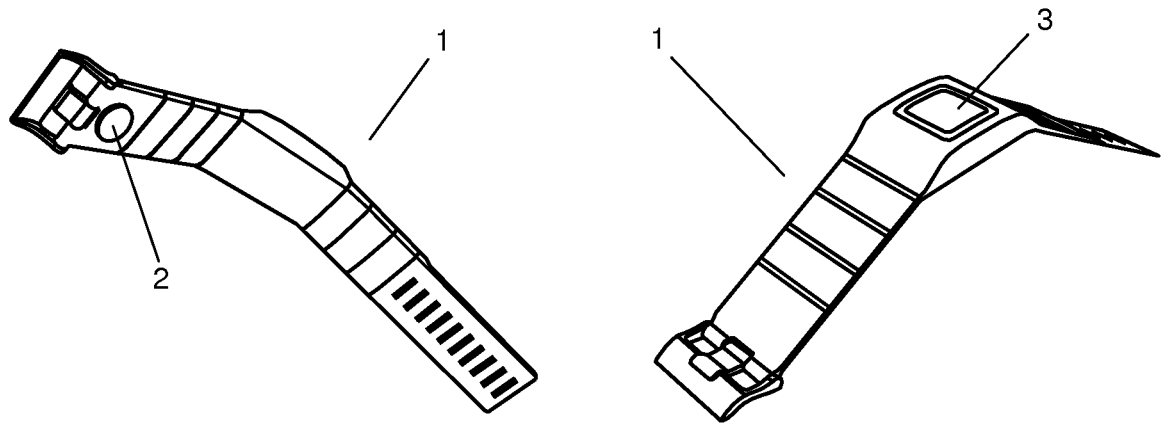
FIG. 5 and FIG. 6 schematically show the design of an exemplary portable device made in the form of a bracelet with sensors that implements the method in accordance with the present invention, whereat FIG. 5 gives the view of the device from its inner side contacting the wrist.

As shown in FIG. 5, the inner side of bracelet 1 carries pulse wave sensor 2 based, for example, on piezoelectric cell. Several pulse sensors may be used to ensure a reliable skin contact with the wrist area where pulse wave signal is detected. Bracelet 1 (see FIG. 6) may have indicator 3 which displays the initial settings and operation mode of the device. The device may also generate a wake-up signal during favorable sleep phase, for example, by means of a vibrator (not shown in the drawings) mounted in bracelet 1. An accelerometer (not shown in the drawings) may be mounted inside bracelet 1 for detecting arm movements of a sleeping person. Pulse wave sensor 2 and the accelerometer are connected to the measuring unit of bracelet 1, which registers pulse wave signals and accelerometer-generated signals. The registered signals are processed in a CPU which can be co-located with the measuring unit in bracelet 1 or made as a separate unit to be attached to human body or carried by person, whereat said CPU receives signals transmitted from the measuring unit by radio or some other means.

The values of RR intervals and respiratory rate are determined in human sleep based on registered pulse wave signal. Since a pulse wave signal is a periodic signal that varies in synchronism with heartbeat, the time intervals between any characteristic points on pulsogram (e.g., peak value of the signal or its derivative) correspond exactly to RR intervals. Instrumental methods for determining heart rate or RR intervals from a pulse wave signal are well known to those skilled in the art. It is also known that, alongside with the above-mentioned periodic variations corresponding to blood filling dynamics at each cardiac cycle, pulse wave signal includes a low frequency component corresponding to respiratory cycle. Instrumental methods of determining the respiratory rate based on low-pass filtering of respiratory component out of pulse wave signal are well known to those skilled in the art.

Thereafter, using the obtained data, i.e., values of RR intervals and respiration rate, the following parameters are periodically measured at in preset time intervals $\Delta t_i$:

$P_1$—the mean value of RR intervals;
$P_2$—the minimum value of RR intervals;
$P_3$—the maximum value of RR intervals;
$P_5$—the mean respiratory rate.

The time interval $\Delta t_i$ over which said parameters are measured is selected in the range from 1 minute to 6 minutes. Here, i is the serial number of i-th time interval.

Furthermore, parameter $P_4$ is determined as the standard deviation of RR intervals over the preceding time interval of 3 minutes to 20 minutes, preferably from 4 minutes to 6 minutes.

The mean number of limb movements $P_6$ over the preceding time interval from 0.5 minutes to 10 minutes, preferably from 4 minutes to 6 minutes, is another parameter needed for final identification of REM sleep phase. Since the occurrence of motor activity is informative by itself for identification of REM sleep, all limb movements detected by accelerometer over a 10 seconds period are taken for one movement.

Thereafter, function value $F(\Delta t_i)$ is determined by formula:

$$F(\Delta t_i) = -K_1 P_1 - K_2 P_2 - K_3 P_3 + K_4 P_4 + K_5 P_5 K_6 P_6,$$

where: $K_1$-$K_6$ are weight coefficients characterizing the contribution of corresponding parameter $P_1$-$P_6$ to the value of $F(\Delta t_i)$.

Table 1 below shows the value ranges of weight coefficients $K_1$-$K_6$, as well optimal value thereof.

TABLE 1

Weight Coefficient Values

| Parameters, units of measurement | Weight coefficients Designation | Weight coefficient values min | max | optimal |
|---|---|---|---|---|
| $P_1$, ms | $K_1$ | 0.6 ms¹ | 3 ms¹ | 1 ms¹ |
| $P_2$, ms | $K_2$ | 0.1 ms¹ | 0.7 ms¹ | 0.14 ms¹ |
| $P_3$, ms | $K_3$ | 0.01 ms¹ | 0.3 ms¹ | 0.03 ms¹ |
| $P_4$, ms | $K_4$ | 0.5 ms¹ | 3 ms¹ | 1.4 ms¹ |
| $P_5$, min⁻¹ | $K_5$ | 1 min | 10 min | 2 min |
| $P_6$ | $K_6$ | 5 | 50 | 22 |

Informative parameters $P_1$-$P_6$ were established, and their weight coefficients $K_1$-$K_6$ for healthy people were obtained experimentally based on polysomnographic clinical studies. Statistically valid methods accepted in medical practice and described, for example, in the article "Polysonmography" (http://www.zonasna.ru/serv002.html) were used for checking the accuracy of REM sleep identification. Weight coefficients $K_1$-$K_6$ were selected so that the function values $F(\Delta t_i)$ in REM and non-REM phases display a maximum difference from each other.

The increment $\Delta F(\Delta t_i)$ of function $F(\Delta t_i)$ over time $\Delta t_i$ is used to identify the onset and termination of REM sleep. If the difference between the current function value $F(\Delta t_i)$ and its previous value $F(\Delta t_{i-1})$ exceeds the first preset threshold value, the onset of REM sleep is identified. If said difference is less than the second preset threshold value, the termination of REM sleep is identified.

Figure 1:
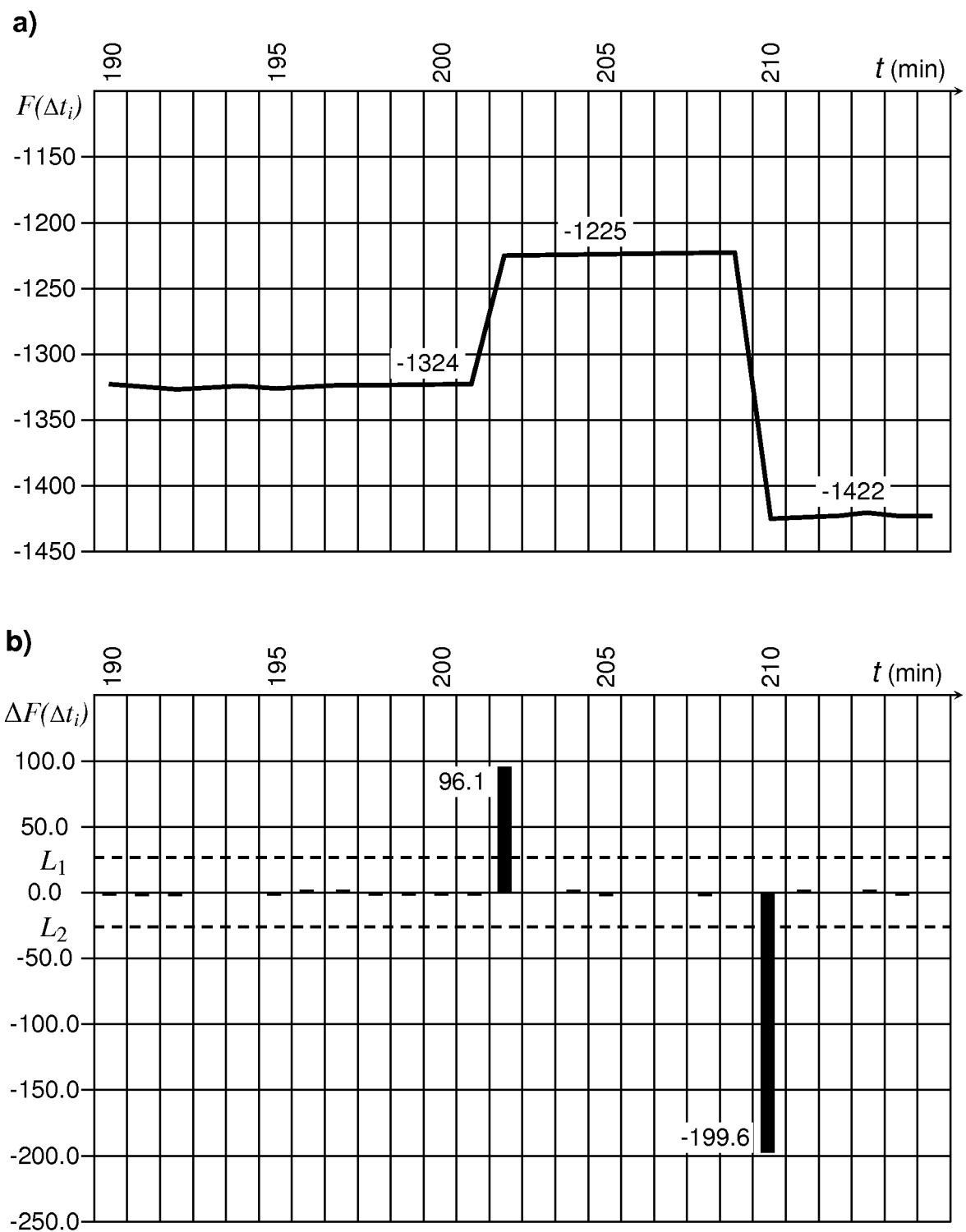
FIG. 1 shows an example of identifying REM sleep phase for one of the test subjects (8VAV), whereat
Figure 2:
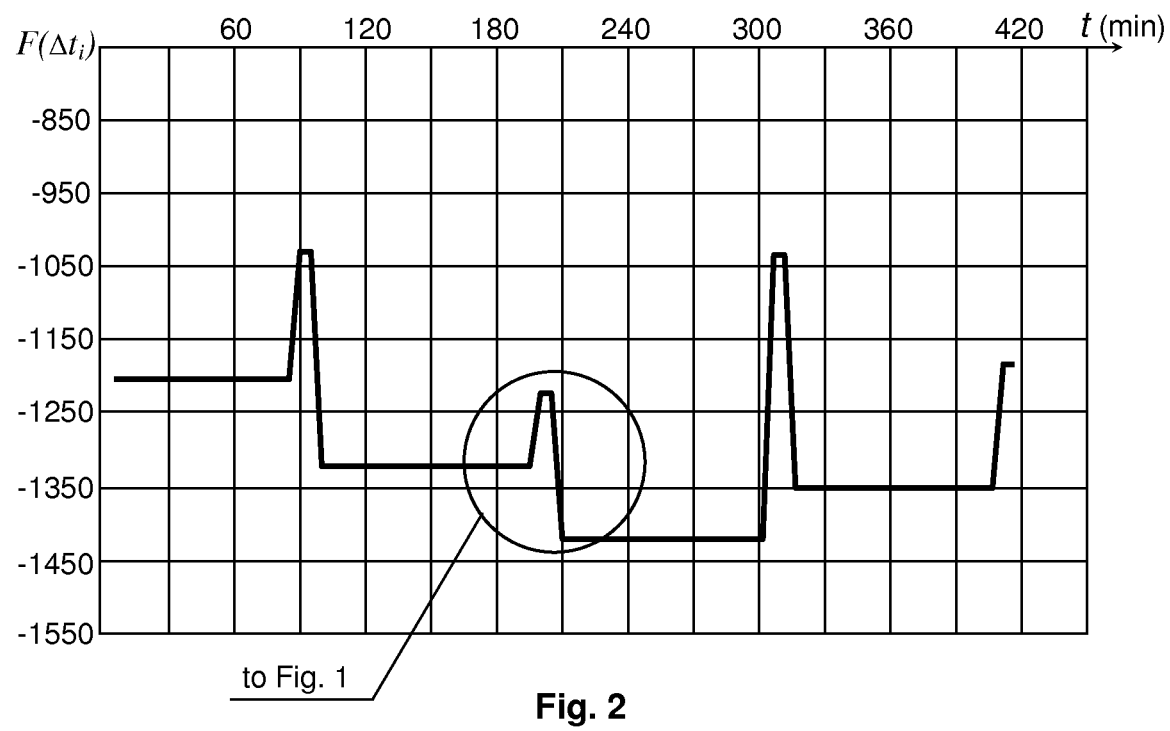
FIG. 2 shows a graph of function $F(\Delta t_i)$ over the entire sleep duration for the same test subject (8VAV) whose sleep is illustrated in FIG. 1, wherein the graph fragment shown in more detail in FIG. 1a is circled.
Figure 3:
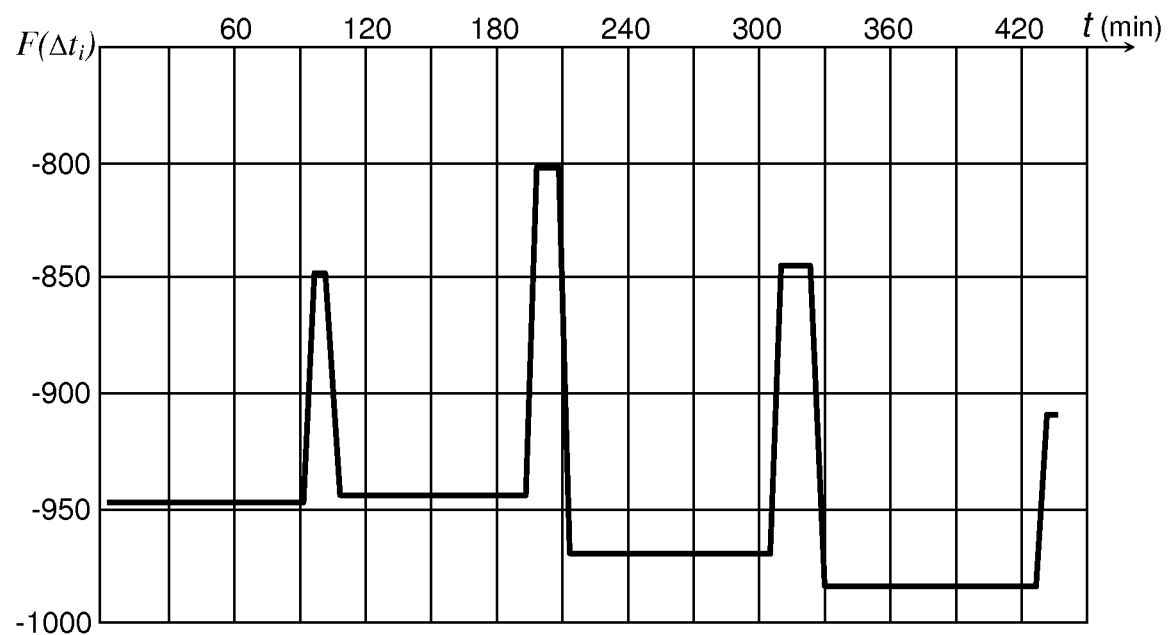
FIG. 3 shows a graph of function $F(\Delta t_i)$ over the entire sleep duration for another test subject (7ESA)
Figure 4:
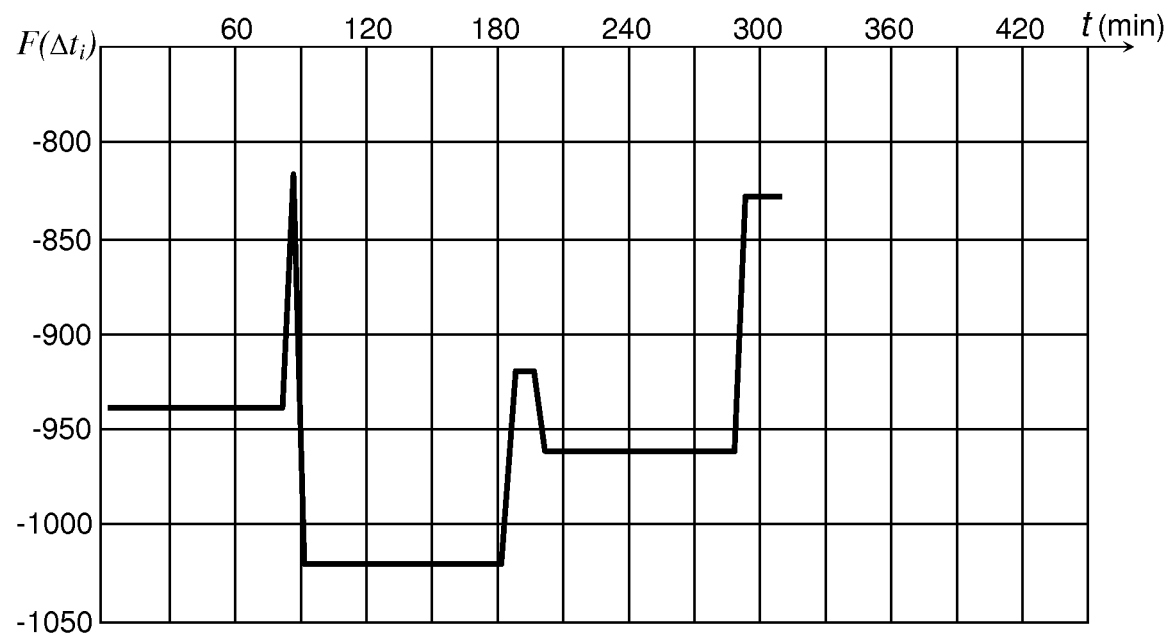
FIG. 4 shows a graph of function $F(\Delta t_i)$ over the entire sleep duration for yet another test subject (3SOR)

FIG. 1-FIG. 4 show examples of function $F(\Delta t_i)$ obtained for different test subjects during their sleep. Optimal weight coefficients $K_1$-$K_6$ given in Table 1 were selected in the course of studies to calculate function values $F(\Delta t_i)$. FIG. 1 FIG. 4 demonstrate a smoothed form of function $F(\Delta t_i)$).

The measuring resolution of accelerometer and pulse wave sensor signals amounted 0.1 in the testing process. All limb movements detected over 10-second time interval were considered to be a single movement and were averaged over the period of 5 min Function values $F(\Delta t_i)$ were calculated every minute, in other words, value $\Delta t_i$ was taken to be 1 minute for each i-th time interval. The first threshold value $L_1$ was selected in the range from 20 to 30, while the second threshold value $L_2$ was selected in the range from $-30$ to $-20$.

FIG. 1a shows a fragment of function $F(\Delta t_i)$) which includes one of REM phases registered during the sleep of one of the test subjects (8VAV). As is seen, function value $F(\Delta t_i)$) rises sharply at 202-th minute of sleep, which indicates the onset of REM sleep, whereas at 210-th minute said function value $F(\Delta t_i)$ falls abruptly, which indicates the termination of REM sleep.

FIG. 1b shows a graph of increment $\Delta F(\Delta t_i)$ of function $F(\Delta t_i)$ from FIG. 1a. As is seen, the increment value $\Delta F(\Delta t_i)$ considerably exceeds the first threshold value $L_1$ with the onset of REM sleep, and becomes noticeably lower than the second threshold value $L_2$ with REM sleep termination.

The example illustrated in FIG. 1 is presented in Table 2 in the form of parameter values $P_1$-$P_6$, function values $F(\Delta t_i)$ and function increment $\Delta F(\Delta t_i)$. The lines with parameter values presented in bold type in Table 2 correspond to REM sleep onset and termination in test subject.

TABLE 2

| Sleep Duration, in min. | $P_1$, ms | $P_2$, ms | $P_3$, ms | $P_4$, ms | $P_5$, min | Number of Movements | $P_6$ over 5 min. | $F(\Delta t_i)$ | $\Delta F(\Delta t_i)$ |
|---|---|---|---|---|---|---|---|---|---|
| 185 | 92 | 1201 | 1422 | — | 14 | 0 | — | — | |
| 186 | 1273 | 1200 | 1421 | — | 15 | 1 | — | — | |
| 187 | 1272 | 1199 | 1420 | — | 15 | 0 | — | — | |
| 188 | 1272 | 1198 | 1418 | — | 15 | 0 | — | — | |
| 189 | 1272 | 1199 | 1418 | 92 | 15 | 0 | 0.2 | −1319 | |
| 190 | 1274 | 1198 | 1419 | 92 | 15 | 0 | 0.2 | −1321 | −1.9 |
| 191 | 1273 | 1201 | 1419 | 94 | 14 | 0 | 0 | −1324 | −3.0 |

TABLE 2-continued

| Sleep Duration, in min. | $P_1$, ms | $P_2$, ms | $P_3$, ms | $P_4$, ms | $P_5$, min | Number of Movements | $P_6$ over 5 min. | $F(\Delta t_i)$ | $\Delta F(\Delta t_i)$ |
|---|---|---|---|---|---|---|---|---|---|
| 192 | 1272 | 1202 | 1421 | 92 | 14 | 0 | 0 | −1326 | −2.0 |
| 193 | 1272 | 1200 | 1422 | 92 | 14 | 0 | 0 | −1326 | 0.3 |
| 194 | 1271 | 1202 | 1421 | 92 | 14 | 0 | 0 | −1325 | 0.8 |
| 195 | 1272 | 1201 | 1421 | 92 | 14 | 0 | 0 | −1326 | −0.9 |
| 196 | 1272 | 1202 | 1422 | 92 | 15 | 0 | 0 | −1324 | 1.8 |
| 197 | 1272 | 1202 | 1420 | 93 | 15 | 0 | 0 | −1323 | 1.5 |
| 198 | 1271 | 1198 | 1422 | 92 | 15 | 0 | 0 | −1323 | 0.1 |
| 199 | 1272 | 1199 | 1421 | 92 | 15 | 0 | 0 | −1324 | −1.1 |
| 200 | 1272 | 1200 | 1418 | 92 | 15 | 0 | 0 | −1324 | 0.0 |
| 201 | 1273 | 1197 | 1418 | 92 | 16 | 0 | 0 | −1322 | 1.4 |
| 202 | 1206 | 1015 | 1290 | 89 | 18 | 0 | 0 | −1226 | 96.1 |
| 203 | 1207 | 1011 | 1290 | 88 | 19 | 0 | 0 | −1226 | 0.2 |
| 204 | 1207 | 1012 | 1290 | 89 | 19 | 0 | 0 | −1225 | 1.3 |
| 205 | 1208 | 1012 | 1290 | 89 | 19 | 0 | 0 | −1226 | −1.0 |
| 206 | 1207 | 1010 | 1290 | 90 | 18 | 0 | 0 | −1225 | 0.7 |
| 207 | 1207 | 1012 | 1290 | 89 | 19 | 0 | 0 | −1225 | 0.3 |
| 208 | 1206 | 1013 | 1290 | 88 | 19 | 0 | 0 | −1225 | −0.5 |
| 209 | 1207 | 1012 | 1290 | 89 | 19 | 0 | 0 | −1225 | 0.5 |
| 210 | 1367 | 1290 | 1500 | 97 | 14 | 1 | 0.2 | −1424 | −199.6 |
| 211 | 1369 | 1300 | 1505 | 98 | 16 | 0 | 0.2 | −1422 | 1.9 |
| 212 | 1369 | 1290 | 1501 | 99 | 15 | 0 | 0.2 | −1421 | 0.9 |
| 213 | 1367 | 1290 | 1498 | 100 | 14 | 0 | 0.2 | −1420 | 1.5 |
| 214 | 1367 | 1285 | 1498 | 99 | 13 | 0 | 0.2 | −1422 | −2.7 |
| 215 | 1367 | 1290 | 1500 | 100 | 15 | 0 | 0 | −1422 | 0.2 |

FIG. 2 is a graph of function $F(\Delta t_i)$ over the entire sleep duration for the same test subject (8VAV). As follows from function values $F(\Delta t_i)$, there occurred four REM phases during the sleep of the test subject.

FIG. 3 shows a graph of function $F(\Delta t_i)$ for another test subject (7ESA). As follows from the graph, four REM phases favorable to awakening were similarly registered during subject's sleep. The subject woke up by himself during the last REM phase.

The number of REM phases may vary during sleep. For example, FIG. 4 shows that three REM phases occurred during the sleep of another test subject (3SOR).

The graph also shows that different REM phases feature different absolute values of function $F(\Delta t_i)$ throughout sleep duration and that REM sleep onset and termination can be reliably identified only by the increment of said function.

A series of tests showed that the method according to the present invention enabled the identification of 73 out of 76 REM sleep phases in 20 test subjects, which testifies to its high reliability of identification of human sleep phase favorable to awakening. The parameters of function $F(\Delta t_i)$ selected therein were also defined by the necessity to use a minimum number of sensors fixed on the wrist to provide comfortable sleeping conditions.

What is claimed is:

1. A method for determining a sleep phase favorable for awakening a person from a sleep, the method comprising:
attaching a motion sensor to an arm or leg of the person, the motion sensor being responsive to movements of the arm or leg;
attaching a pulse wave sensor to a wrist or a forearm of the person, the pulse wave sensor being responsive to vascular blood filling of an area of the wrist or forearm;
providing a measuring unit to which the motion sensor and the pulse wave sensor are connected;
registering by the measuring unit signals from the pulse wave sensor and signals from the motion sensor;
sending the signals from the pulse wave sensor and the signals from the motion sensor registered by the measuring unit to a CPU, operably associated with the measuring unit, for processing;
calculating, by the CPU, values of RR intervals and a respiratory rate of the person, wherein RR intervals represent intervals between successive heartbeats, using the signals from the pulse wave sensor registered by the measuring unit;
calculating, by the CPU, a number of movements of the arm or leg of the person using the signals from the motion sensor registered by the measuring unit;
determining, by the CPU, a mean value $P_1$ of the RR intervals over a time interval $\Delta t_i$, wherein i is a serial number of the time interval $\Delta t_i$;
determining, by the CPU, a minimal value $P_2$ of the RR intervals over the time interval $\Delta t_i$;
determining, by the CPU, a maximal value $P_3$ of the RR intervals over the time interval $\Delta t_i$;
determining, by the CPU, a standard deviation value $P_4$ of the RR intervals over a preceding time interval of 3 to 20 min;
determining, by the CPU, a mean value $P_5$ of the respiratory rate over the time interval $\Delta t_i$;
determining, by the CPU, an average number $P_6$ of the arm or leg movements over a preceding time interval ranging from 0.5 to 10 minutes;
evaluating, by the CPU, function values $F(\Delta t_i)$ over preset time intervals $\Delta t_i$, wherein:

$$F(\Delta t_i) = K_1 P_1 - K_2 P_2 - K_3 P_3 + K_4 P_4 + K_5 P_5 + K_6 P_6, \text{ and}$$
wherein $K_1$-$K_6$ are weight coefficients characterizing contribution of parameters $P_1$-$P_6$ to the values of the function $F(\Delta t_i)$;
evaluating, by the CPU, increment values of the function $F(\Delta t_i)$ over the time intervals $\Delta t_i$;
comparing, by the CPU, the increment values of the function $F(\Delta t_i)$ over the time intervals $\Delta t_i$ with a preset threshold value;
determining, by the CPU, onset and/or termination of a sleep phase favorable for awakening a person from a sleep based on comparison between the increment values of the function $F(\Delta t_i)$ over the time intervals $\Delta t_i$ and a preset threshold value;

outputting a signal by the CPU during the sleep phase favorable for awakening a person from a sleep to a vibrator based on comparison between the increment values of the function $F(\Delta t_i)$ over the time intervals $\Delta t_i$ and a preset threshold value, and generating by the vibrator a wake-up signal based on the signal outputted by the CPU during the sleep phase determined as favorable for awakening a person from a sleep based on comparison between the increment values of the function $F(\Delta t_i)$ over the time intervals $\Delta t_i$ and a preset threshold value.

2. The method of claim 1, further comprising selecting the time interval over which the value of $P_4$ is calculated in a range from 4 to 6 minutes.

3. The method of claim 1, further comprising selecting the time interval over which the number $P_6$ is calculated in a range from 4 to 6 minutes.

4. The method of claim 1, wherein:
a value of $K_1$ is selected in a range from 0.6 to 3 ms$^{-1}$;
a value of $K_2$ is selected in a range of 0.1 to 0.7 ms$^{-1}$;
a value of $K_3$ is selected in a range of from 0.01 to 0.3 ms$^{-1}$;
a value of $K_4$ is selected in a range from 0.5 to 3 ms$^{-1}$;
a value of $K_5$ is selected in a range from 1 to 10 min; and
a value of $K_6$ is selected in a range from 5 to 50.

5. The method of claim 4, further comprising selecting the value of $K_1$ in a range from 0.9 to 1.05 ms$^{-1}$.

6. The method of claim 4, further comprising selecting the value of $K_2$ in a range from 0.1 to 0.2 ms$^{-1}$.

7. The method of claim 4, further comprising selecting the value of $K_3$ in a range from 0.02 to 0.05 ms$^{-1}$.

8. The method of claim 4, further comprising selecting the value of $K_4$ in a range from 1.3 to 1.5 ms$^{-1}$.

9. The method of claim 4, further comprising selecting the value of $K_5$ in a range from 1.5 to 2.3 min.

10. The method of claim 4, further comprising selecting the value of $K_6$ in a range from 18 to 24.

11. The method of claim 1, wherein the pulse wave sensor-comprises a piezoelectric sensor, a strain gauge, or an optical sensor.

12. The method of claim 1, wherein the motion sensor comprises an accelerometer.

13. The method of claim 1, wherein the time intervals $\Delta t_i$ are selected in a range from 1 to 6 minutes.

14. The method of claim 1, further comprising identifying the onset of a sleep phase favorable for awakening a person from a sleep if the increment of the function $F(\Delta t_i)$ over the time interval $\Delta t_i$ exceeds the preset threshold value.

15. The method of claim 1, further comprising identifying the termination of a sleep phase favorable for awakening a person from a sleep if the increment of the function $F(\Delta t_i)$ over the time interval $\Delta t_i$ is smaller than the preset threshold value.

* * * * *